(12) United States Patent
Bernardon et al.

(10) Patent No.: US 6,171,603 B1
(45) Date of Patent: Jan. 9, 2001

(54) BIOAROMATIC AMIDO COMPOUNDS AND PHARMACEUTICAL/COSMETIC COMPOSITIONS COMPRISED THEREOF

(75) Inventors: Jean-Michel Bernardon, Le Rouret; Laurence Vigne, Antibes, both of (FR)

(73) Assignee: Centre International de Recherches Dermatologiques Galderma, Valbonne (FR)

( * ) Notice: Under 35 U.S.C. 154(b), the term of this patent shall be extended for 0 days.

(21) Appl. No.: 09/246,715

(22) Filed: Feb. 9, 1999

Related U.S. Application Data

(62) Division of application No. 08/605,960, filed on Feb. 23, 1996, now Pat. No. 5,935,585.

(30) Foreign Application Priority Data

Feb. 23, 1995 (FR) .................................. 95-02133

(51) Int. Cl.[7] ................. A61K 31/167; A61K 31/196; A61K 31/245
(52) U.S. Cl. ............... 424/401; 514/535; 514/563; 514/617; 514/621; 514/622
(58) Field of Search ................ 514/617, 621, 514/622, 535, 563; 424/401

(56) References Cited

FOREIGN PATENT DOCUMENTS

| 0227431 | 7/1987 | (EP) . |
| 0514264 | 11/1992 | (EP) . |
| 0661260 | 7/1995 | (EP) . |
| 92/06948 | 4/1992 | (WO) . |

Primary Examiner—Richard L. Raymond
(74) Attorney, Agent, or Firm—Burns, Doane, Swecker & Mathis, L.L.P.

(57) ABSTRACT

Novel pharmaceutically/cosmetically-active biaromatic amido compounds have the structural formula (I):

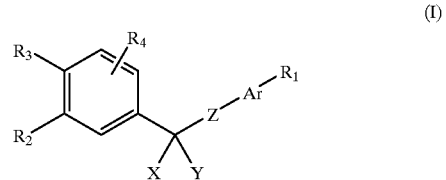

(I)

in which Ar is a radical selected from among those of the following formulae (a)–(e):

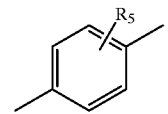

(a)

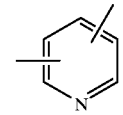

(b)

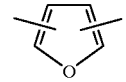

(c)

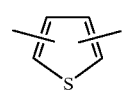

(d)

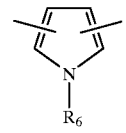

(e)

and are useful for the treatment of a wide variety of disease states, whether human or veterinary, for example dermatological, rheumatic, respiratory, cardiovascular and ophthalmological disorders, as well as for the treatment of mammalian skin and hair conditions/disorders.

21 Claims, 2 Drawing Sheets

BIOAROMATIC AMIDO COMPOUNDS AND PHARMACEUTICAL/COSMETIC COMPOSITIONS COMPRISED THEREOF

This application is a divisional of application Ser. No. 08/605,960, filed Feb. 23, 1996, now U.S. Pat. No. 5,935,585.

BACKGROUND OF THE INVENTION

TECHNICAL FIELD OF THE INVENTION

The present invention relates to novel amide-derived biaromatic compounds and to pharmaceutical/cosmetic compositions comprised thereof; the subject amido compounds are especially useful in human or veterinary medicine, or alternatively in cosmetic compositions.

SUMMARY OF THE INVENTION

The compounds according to the invention display marked activity in the fields of cell differentiation and proliferation, and are particularly useful in the topical and systemic treatment of dermatological conditions associated with a keratinization disorder, dermatological conditions (and the like) including an inflammatory and/or immunoallergic component, and dermal or epidermal proliferations, whether benign or malignant. The subject compounds can, in addition, be used for the treatment of degeneration diseases of the connective tissue, for combating skin aging, whether photoinduced or chronologic, and for treating cicatrization disorders. They are also useful for ophthalmological applications, especially for the treatment of corneopathies.

The compounds according to this invention are also useful for the treatment of osteoporosis, and for the treatment of viral diseases, as well as for the treatment of any condition associated with hypervitaminose A. In general, they are useful for the treatment of any disease state which is associated with a modification of the expression of receptors belonging to the superfamily of steroid and thyroid hormone receptors.

Too, the compounds according to the invention can be formulated into cosmetic compositions for body and hair care.

Briefly, the biaromatic amido compounds according to the invention have the following structural formula (I):

(I)

in which Ar is a radical selected from among those of the following formulae (a)–(e):

(a)

(b)

(c)

(d)

(e)

in which $R_5$ and $R_6$ are as defined below; Z is —CO—$NR_7$—; $R_1$ is (i) a —$CH_3$ radical, (ii) a radical —$CH_2$—O—$R_6$, (iii) a radical —O—$R_6$, (iv) a radical —CO—$R_8$ or (v) a radical —S(O)$_t R_9$, wherein $R_6$, $R_8$, $R_9$ and t are as defined below; X and Y may be taken separately, in which event X is a hydrogen atom or a lower alkyl radical, and Y is a radical of the formula —$(CH_2)_n$—$CH_3$ or of the formula —$(CH_2)_n$—$R_{10}$, or X and Y may be taken together, in which event X and Y together form, with the carbon atom from which they depend, a single radical containing a double bond, selected from among those of the formulae =N—O—$(CH_2)_n$—$R_{10}$, =CH—$(CH_2)_m$—$R_{10}$, =N—O—$(CH_2)_2$—O—$CH_2$—$CH_3$, =N—O—$CH_2$—O—$CH_2$—$CH_2$—O—$CH_3$, and =CH—$(CH_2)_m$—$CH_3$, wherein $R_{10}$, m and n are as defined below; $R_2$ and $R_3$, taken separately, are each a hydrogen atom, a linear or branched alkyl radical having from 1 to 20 carbon atoms, a radical —$OR_6$ or a radical —$SR_6$, wherein $R_6$ is as defined below, with the proviso that $R_2$ and $R_3$ cannot simultaneously be a hydrogen atom, a radical —$OR_6$ or a radical —$SR_6$, or $R_2$ and $R_3$ together form, with the adjacent aromatic ring from which they depend, a 5- or 6-membered ring optionally substituted by methyl radicals and/or optionally interrupted by an oxygen or sulfur atom or by an —SO— or —$SO_2$— radical; $R_4$ is a hydrogen atom, a halogen atom, a lower alkyl radical or a radical —$OR_6$, wherein $R_6$ is as defined below, with the proviso that $R_5$ has the same definition as $R_4$; $R_6$ is a hydrogen atom, a linear or branched alkyl radical having from 1 to 20 carbon atoms or a radical —CO—$R_{11}$, wherein $R_{11}$ is as defined below; $R_7$ is a hydrogen atom or a lower alkyl radical; $R_8$ is (a) a hydrogen atom, (b) a lower alkyl radical, (c) a radical of the formula:

wherein R' and R" are as defined below, or (d) a radical —$OR_{12}$, wherein $R_{12}$ is as defined below; $R_9$ and $R_{11}$, which may be identical or different, are each a lower alkyl radical; $R_{10}$ is (i) a radical —$OR_6$, (ii) a radical —CO—$R_8$, (iii) a radical of the formula:

wherein R' and R" are as defined below, (iv) an optionally substituted aryl radical, (v) a heterocyclic radical, or (vi) a $C_3$ or $C_6$ cycloaliphatic radical; $R_{12}$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; R' and R", which may be identical or different, are each a hydrogen atom, a lower alkyl radical, a mono or polyhydroxyalkyl radical, an optionally substituted aryl radical or an amino acid or peptide or sugar residue with the proviso that R' and R" may together form, with the nitrogen atom from which they depend, a heterocycle; m is an integer ranging from 1 to 20; n is an integer ranging from 2 to 20; and t is an integer equal to 0, 1 or 2.

This invention also features the salts of the compounds of formula (I) in the event that $R_1$ is a carboxylic acid functional group, as well as the optical and geometric isomers thereof. When the compounds according to the invention are in the form of salts, they are preferably salts of an alkali or alkaline earth metal, or alternatively, of zinc or of an organic amine.

BRIEF DESCRIPTION OF THE DRAWINGS

The SCHEMATICS IN FIGS. 1 and 2 set forth reaction schemes/mechanisms illustrating syntheses for the preparation of the biaromatic amido compounds according to the present invention.

DETAILED DESCRIPTION OF BEST MODE AND PREFERRED EMBODIMENTS OF THE INVENTION

More particularly according to the present invention, by "lower alkyl radical" is intended an alkyl radical having from 1 to 6 carbon atoms, preferably methyl, ethyl, isopropyl, butyl, tert-butyl and hexyl radicals.

By "linear or branched alkyl radical having from 1 to 20 carbon atoms" is preferably intended methyl, ethyl, propyl, 2-ethylhexyl, octyl, dodecyl, hexadecyl and octadecyl radicals.

By "monohydroxyalkyl radical" is intended a radical preferably having 2 or 3 carbon atoms, especially a 2-hydroxyethyl, 2-hydroxypropyl or 3-hydroxypropyl radical.

By "polyhydroxyalkyl radical" is intended a radical preferably having 3 to 6 carbon atoms and 2 to 5 hydroxyl groups, such as 2,3-dihydroxypropyl, 2,3,4-trihydroxybutyl or 2,3,4,5-tetrahydroxypentyl radicals, or a pentaerythritol residue.

By "aryl radical" is preferably intended a phenyl radical optionally substituted by at least one halogen atom, or at least one hydroxyl or nitro functional group.

By "aralkyl radical" is preferably intended a benzyl or phenethyl radical optionally substituted by at least one halogen atom, or at least one hydroxyl or nitro functional group.

By "alkenyl radical" is intended a radical preferably having from 1 to 5 carbon atoms and one or more sites of ethylenic unsaturation, such as, more particularly, the allyl radical.

By "sugar residue" is intended a residue derived especially from glucose, galactose or mannose, or alternatively from glucuronic acid.

By "amino acid residue" is especially intended a residue derived from lysine, glycine or aspartic acid, and by "peptide residue" is more particularly intended a dipeptide or tripeptide residue prepared via the combination of amino acids.

By "$C_3$ or $C_6$ cycloaliphatic radical" is more particularly intended a cyclopropyl or cyclohexyl radical.

Lastly, by "heterocycle" is preferably intended a piperidino, morpholino, pyrrolidino or piperazino radical, optionally substituted at the 4-position by a $C_1$–$C_6$ alkyl radical or a mono- or polyhydroxyalkyl radical as defined above.

When $R_4$ and $R_5$ represent a halogen atom, it is preferably a fluorine, chlorine or bromine atom.

Among the compounds of formula (I) according to the present invention, particularly representative are the following:

anti-4-[α-Hydroxyhexylimino-(5,6,7,8-tetrahydro-5,5,8,8-tetramethyl-2-naphthyl)acetamido]benzoic acid;

syn-4-[α-Hydroxyhexylimino-(5,6,7,8-tetrahydro-5,5,8,8-tetramethyl-2-naphthyl)acetamido]benzoic acid;

syn-4-[α-Methoxycarbonylpentylimino-(5,6,7,8-tetrahydro-5,5,8,8-tetramethyl-2-naphthyl)acetamido]benzoic acid;

syn-4-[α-Hydroxyoctyloxyimino-(5,6,7,8-tetrahydro-5,5,8,8-tetramethyl-2-naphthyl)acetamido]benzoic acid;

trans-4-[α-Hydroxyoctyloxyimino-(5,6,7,8-tetrahydro-5,5,8,8-tetramethyl-2-naphthyl)acetamido]benzoic acid;

syn-4-[α-Hydroxyheptyloxyimino-(5,6,7,8-tetrahydro-5,5,8,8-tetramethyl-2-naphthyl)acetamido]benzoic acid;

trans-4-[α-Hydroxyheptyloxyimino-(5,6,7,8-tetrahydro-5,5,8,8-tetramethyl-2-naphthyl)acetamido]benzoic acid;

syn-4-[α-Hydroxypropyloxyimino-(5,6,7,8-tetrahydro-5,5,8,8-tetramethyl-2-naphthyl)acetamido]benzoic acid;

trans-4-[α-Hydroxypropyloxyimino-(5,6,7,8-tetrahydro-5,5,8,8-tetramethyl-2-naphthyl)acetamido]benzoic acid;

syn-4-[α-Ethoxycarbonylpropyloxyimino-(5,6,7,8-tetrahydro-5,5,8,8-tetramethyl-2-naphthyl)acetamido]benzoic acid;

syn-4-[α-Hydroxydecyloxyimino-(5,6,7,8-tetrahydro-5,5,8,8-tetramethyl-2-naphthyl)acetamido]benzoic acid;

syn-4-[α-Hydroxynonyloxyimino-(5,6,7,8-tetrahydro-5,5,8,8-tetramethyl-2-naphthyl)acetamido]benzoic acid;

syn-4-[α-Benzyloxyimino-(5,6,7,8-tetrahydro-5,5,8,8-tetramethyl-2-naphthyl)acetamido]benzoic acid;

syn-4-[α-Methoxyethoxymethoxyimino-(5,6,7,8-tetrahydro-5,5,8,8-tetramethyl-2-naphthyl)acetamido]benzoic acid;

Allyl syn-4-[α-ethoxycarbonylpropyloxyimino-(5,6,7,8-tetrahydro-5,5,8,8-tetramethyl-2-naphthyl)acetamido]benzoate;

(E)-4-[2-(5,6,7,8-Tetrahydro-5,5,8,8-tetramethyl-2-naphthyl)-2-nonenamido]benzoic acid;

(Z)-4-[2-(5,6,7,8-Tetrahydro-5,5,8,8-tetramethyl-2-naphthyl)-2-nonenamido]benzoic acid;

(E)-4-[2-(5,6,7,8-Tetrahydro-5,5,8,8-tetramethyl-2-naphthyl)-2-undecenamido]benzoic acid;

(E)-4-[2-(5,6,7,8-Tetrahydro-5,5,8,8-tetramethyl-2-naphthyl)-2-undecenamido]phenylcarboxamide;

(E)-4-[2-(5,6,7,8-Tetrahydro-5,5,8,8-tetramethyl-2-naphthyl)-2-undecenamido]benzenemethanol;

(E)-4-[2-(5,6,7,8-Tetrahydro-5,5,8,8-tetramethyl-2-naphthyl)-2-undecenamido]phenol;

(Z)-4-[2-(5,6,7,8-Tetrahydro-5,5,8,8-tetramethyl-2-naphthyl)-2-undecenamido]benzoic acid;

(E)-4-[2-(5,6,7,8-Tetrahydro-5,5,8,8-tetramethyl-2-naphthyl)-2-hexadecenamido]benzoic acid;

(Z)-4-[2-(5,6,7,8-Tetrahydro-5,5,8,8-tetramethyl-2-naphthyl)-2-hexadecenamido]benzoic acid.

According to the present invention, the compounds of formula (I) which are more particularly preferred are those in which $R_1$ represents the radical —$COR_8$, and X and Y together form, with the carbon atom from which depend, a radical selected from among those of the following formulae:

wherein $R_8$, $R_{10}$, m and n are as defined above.

The present invention also features the processes for preparing the compounds of formula (I) via the reaction schemes described below and illustrated in the FIGS. 1 and 2 of the Drawings.

Figure 1:
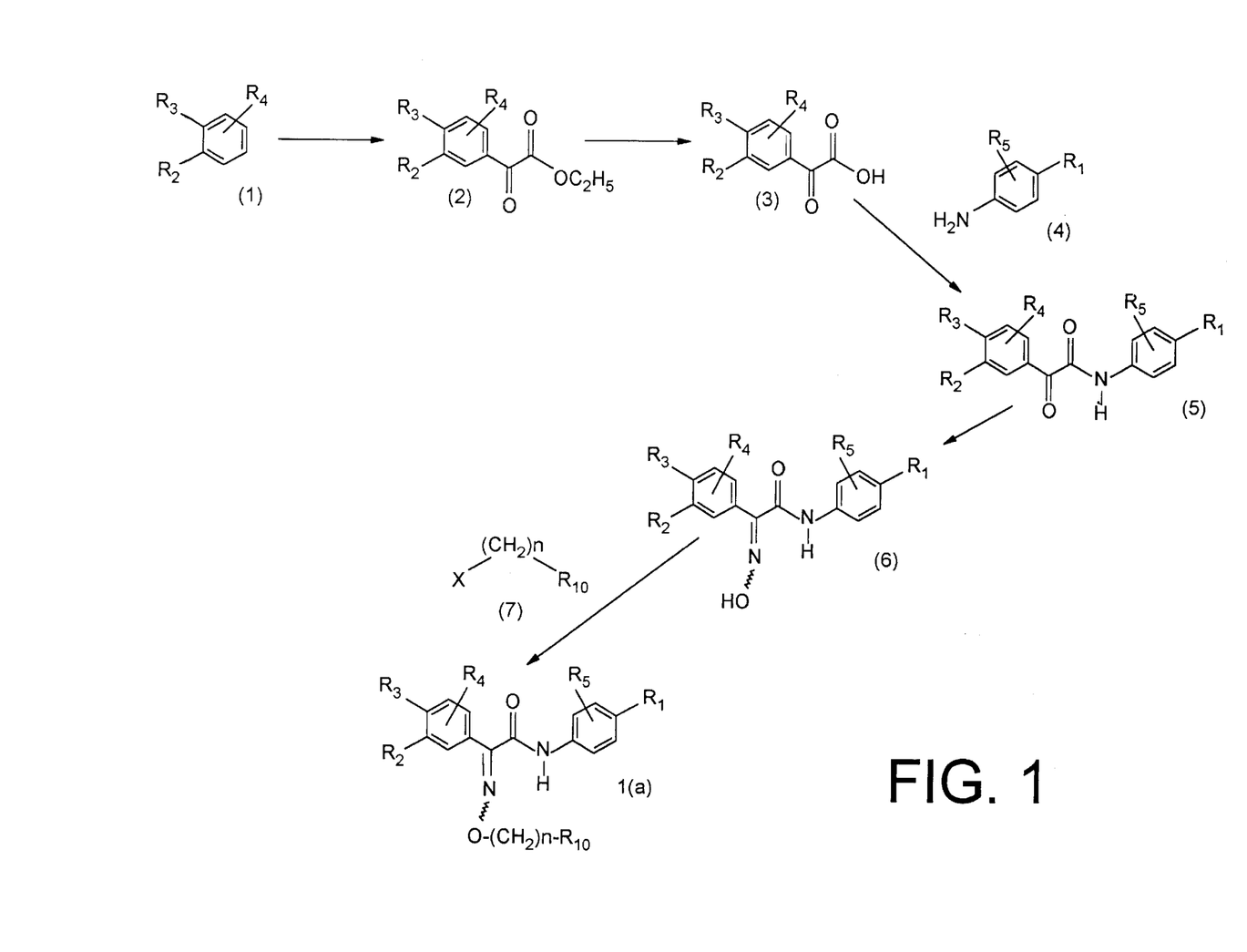
Figure 2:
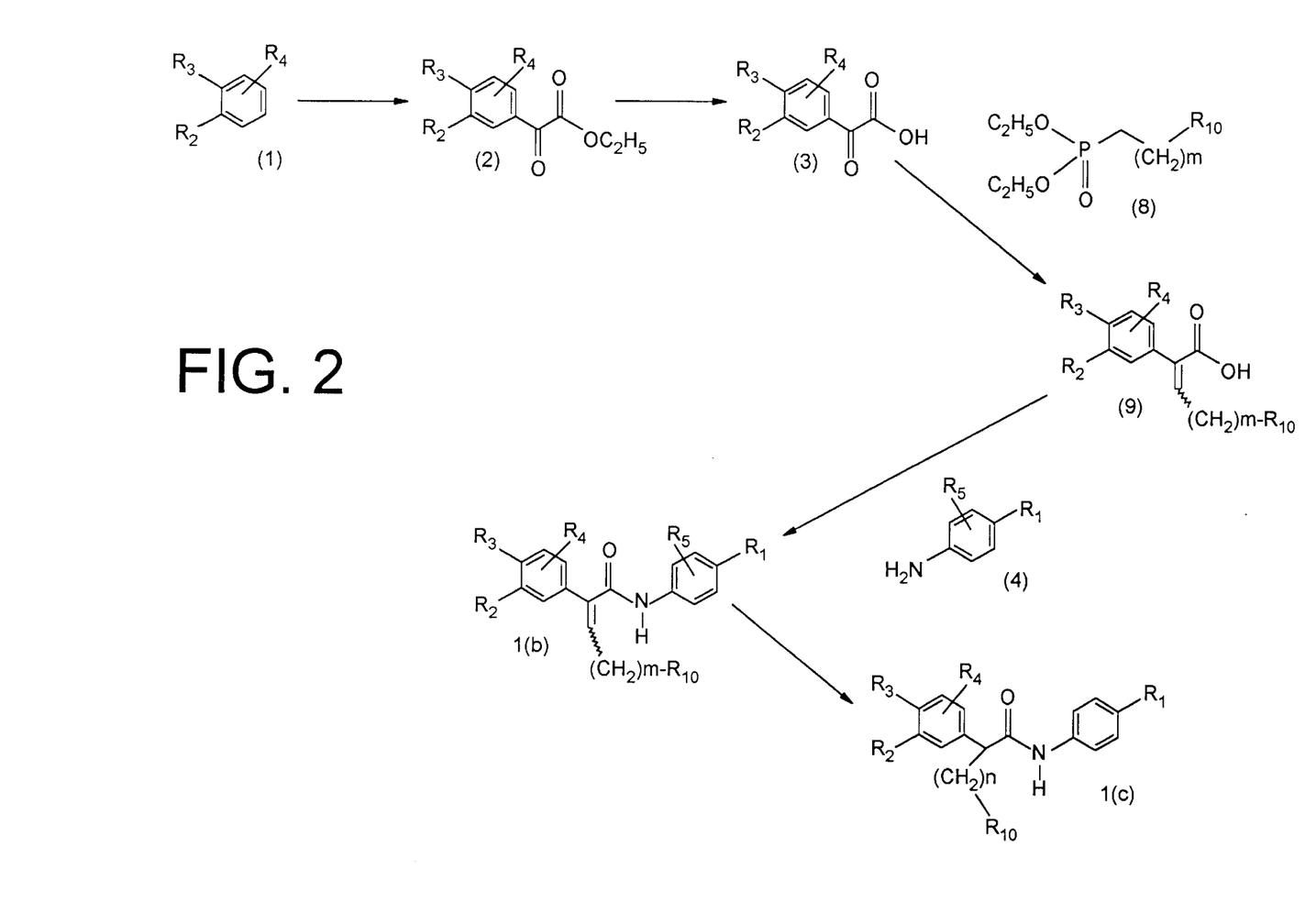

The derivatives of formula (1a) can be prepared by a series of reactions shown in FIG. 1, first comprising a Friedel-Crafts type reaction between the aromatic compound of formula (1) and the ethoxallyl chloride in the presence of a Lewis acid such as $AlCl_3$, followed by saponification of the ester functional group in the presence of a base, such as sodium or lithium hydroxide, in an alcoholic solvent or THF. The derivative of formula (3) thus obtained is coupled with the aniline of formula (4) either via the acid chloride or in the presence of dicyclohexylamine and dimethylaminopyridine in a solvent such as THF or dichloromethane. By reacting the compound of formula (5) with hydroxylamine in an alcoholic solvent such as ethyl alcohol, the compound of formula (6) is obtained which is then alkylated by a halogenated compound of formula (7), preferably iodine- or bromine-containing, either via its sodium-containing derivative in DMF, or in the presence of potassium carbonate in a solvent such as methyl ethyl ketone. The derivatives of formula (1b) can be prepared by a series of reactions, shown in FIG. 2, entailing a Horner-Emmons type reaction between the glyoxylic compound of formula (3) and a phosphonate of formula (8). The derivative of formula (9) thus obtained is then coupled with the aniline of formula (4) either via the acid chloride or in the presence of dicyclohexylamine and of dimethylaminopyridine in a solvent such as THF or dichloromethane.

The derivatives of formula I(c) can be obtained from the compound of formula I(b) by hydrogenation utilizing a catalyst such as palladium on carbon in a solvent such as dioxane or ethyl alcohol.

When $R_1$ represents the —COOH radical, the compounds are preferably prepared by protecting $R_1$ with an allyl, benzyl or tert-butyl type protecting group. The conversion into the free form can be carried out:

(1) in the event of an allyl type protecting group, by means of a catalyst such as certain transition metal complexes, for example tetrakis(triphenylphosphine)palladium(0), in the presence of a secondary amine such as morpholine or the sodium salt of diethyl malonate;

(2) in the event of a benzyl type protecting group, by debenzylation in the presence of hydrogen, by means of a catalyst such as palladium on carbon, in an alcoholic solvent such as ethyl alcohol or in dioxane;

(3) in the event of a tert-butyl type protecting group, by means of trimethylsilane iodide or of trifluoroacetic acid, in a solvent such as dichloromethane.

The present invention also features therapeutic/pharmaceutical applications of the compounds of formula (I).

Depending on the nature of the particular radicals selected, these compounds exhibit either an agonist activity in the test for differentiation of mouse embryonic teratocarcinoma cells (F9) (*Cancer Research,* 43, p. 5268 (1983)) and/or in the test for inhibition of ornithine decarboxylase after induction with TPA in mice (*Cancer Research,* 38, p. 793–801 (1978)) or, on the other hand, an antagonist activity with respect to the expression of one or more biological markers in the test for differentiation of mouse embryonic teratocarcinoma cells (F9) (*Skin Pharmacol.,* 3, pp. 156–267 (1990)) and/or on the in vitro differentiation of human keratinocytes (*Anal. Biochem.,* 192, pp. 232–236 (1991)).

The compounds according to the invention are particularly suitable in the following fields of therapy:

(1) for treating dermatological conditions associated with a keratinization disorder related to differentiation and to proliferation, especially for treating acne vulgaris or comedo-type, polymorphic or rosacea acnes, nodulocystic acne or acne conglobata, senile acnes, secondary acnes such as solar acne, acne medicamentosa or occupational acne;

(2) for treating other types of keratinization disorders, especially ichthyoses, ichthyosiform states, Darier's disease, keratoses palmaris and plantaris, leucoplakias and leucoplakia-like states, skin or mucous (buccal) lichen;

(3) for treating other dermatological conditions associated with a keratinization disorder manifesting an inflammatory and/or immunoallergic component, and, especially, all forms of psoriasis, whether cutaneous, mucous or ungual, and even arthropathic psoriasis, or, alternatively, skin atopy, such as eczema or respiratory atopy or alternatively gingival hypertrophy; the compounds can also be used for treating inflammatory conditions not exhibiting keratinization disorder;

(4) for treating all dermal or epidermal proliferations, whether benign or malignant, whether or not they are of viral origin, such as verruca vulgaris, verruca plana and epidermodysplasia verruciformis, oral or florid papillomatoses and proliferations which can be induced by ultraviolet radiation, especially in the case of baso- and spinocellular epitheliomas;

(5) for treating other dermatological disorders such as bullous dermatoses and collagen diseases;

(6) for treating certain ophthalmological disorders, especially corneopathies;

(7) for repairing or combating skin aging, whether photoinduced or chronologic, or to reduce pigmentations and actinic keratoses, or all pathologies associated with chronologic or actinic aging;

(8) for preventing or curing the stigmas of epidermal and/or dermal atrophy induced by local or systolic corticosteroids, or any other form of skin atrophy;

(9) for preventing or treating cicatrization disorders or for preventing or for repairing vibices;

(10) for combating disorders of the sebaceous function, such as acne hyperseborrhoea or simple seborrhoea;

(11) for the treatment or prevention of cancerous or precancerous states;

(12) for the treatment of inflammatory conditions such as arthritis;

(13) for the treatment of any condition of viral origin at the level of the skin or in general;

(14) for the prevention or treatment of alopecia;

(15) for the treatment of dermatological or general conditions including an immunological component;

(16) for the treatment of conditions of the cardiovascular system, such as arteriosclerosis;

(17) for the treatment or prevention of osteoporosis;

(18) for the treatment of seasonally-related depression.

For the aforesaid therapeutic or pharmaceutical applications, the compounds according to the invention can advantageously be used in combination with other compounds displaying retinoid-type activity, with the D vitamins or derivatives thereof, with corticosteroids, with anti-free radical agents, with α-hydroxy or α-keto acids or derivatives thereof, or alternatively with ion channel blockers. By "D vitamins or derivatives thereof" are intended, for example, the derivatives of vitamin $D_2$ or $D_3$ and in particular 1,25-dihydroxyvitamin $D_3$. By "anti-free radical agents" are intended, for example, α-tocopherol, superoxide dismutase, ubiquinol or certain metal-chelating agents. By "α-hydroxy or α-keto acids or derivatives thereof" are intended, for example, lactic, malic, citric, glycolic, mandelic, tartaric, glyceric or ascorbic acids or salts, amides or esters thereof. By "ion channel blockers" are intended, for example, minoxidil (2,4-diamino-6-piperidinopyrimidine 3-oxide) and derivatives thereof.

The present invention thus also features medicinal compositions containing at least one compound of formula (I), one of its optical or geometric isomers, or one of its pharmaceutically acceptable salts or other derivatives thereof.

The pharmaceutical/therapeutic compositions of this invention, intended especially for the treatment of the aforesaid disease states comprise a carrier, diluent or vehicle which is pharmaceutically acceptable and compatible with the mode or regime of administration selected for the given composition, at least one compound of formula (I), one of its optical or geometric isomers or one of the salts, etc., thereof.

The administration of the compounds according to the invention can be carried out systemically, enterally, parenterally, topically or ocularly.

For enteral administration, the medicinal/pharmaceutical compositions may be in the form of tablets, gelatin capsules, sugar-coated tablets, syrups, suspensions, solutions, elixirs, powders, granules, emulsions, microspheres or nanospheres or lipid or polymeric vesicles which permit a controlled release. For parenteral administration, the compositions may be in the form of solutions or suspensions for perfusion or for injection.

The compounds according to the invention are generally administered at a daily dose of about 0.01 mg/kg to 100 mg/kg of body weight, and this at the regime or rate of 1 to 3 doses per diem.

For topical administration, the pharmaceutical compositions based on compounds according to the invention are more particularly intended for the treatment of the skin and the mucous membranes and can be provided in the form of ointments, creams, milks, pommades, powders, impregnated pads, solutions, gels, sprays, lotions or suspensions. They may also be provided in the form of microspheres or nanospheres or lipid or polymeric vesicles or polymeric patches and hydrogels which permit a controlled release.

These compositions for topical administration may, moreover, be provided either in anhydrous form or in an aqueous form according to the particular clinical indication.

For ocular administration, they are principally collyria.

These compositions for topical or ocular application contain at least one compound of formula (I), or one of its optical or geometric isomers or, alternatively, one of its salts, etc., at a concentration preferably ranging from 0.001% to 5% by weight relative to the total weight of the composition.

The compounds of formula (I) according to the invention also find application in the cosmetic field, in particular for body and hair care and especially for the treatment of skins with acne tendency, for hair regrowth, against loss, for combating the greasy appearance of the skin or the hair, in the protection against the harmful effects of the sun or in the treatment of physiologically dry skins, for preventing and/or for combating photoinduced or chronologic aging.

For cosmetic applications, the compositions of the invention may, moreover, be advantageously used in combination with other compounds displaying retinoid-type activity, with the D vitamins or derivatives thereof, with corticosteroids, with anti-free radical agents, with α-hydroxy or α-keto acids or derivatives thereof, or alternatively with ion channel blockers, all of these different active agents being as defined above.

The present invention therefore also features cosmetic compositions comprising a carrier, diluent or vehicle which is cosmetically acceptable and suitable for a topical application, at least one compound of formula (I) or one of its optical or geometric isomers or one of its salts. Such cosmetic compositions are advantageously presented in the form of a cream, a milk, a lotion, a gel, microspheres or nanospheres or lipid or polymeric vesicles, a soap or a shampoo.

The concentration of the compound of formula (I) in the cosmetic compositions according to the invention advantageously ranges from 0.001% to 3% by weight relative to the total composition.

The medicinal and cosmetic compositions according to the invention may, in addition, contain inert or even pharmacodynamically or cosmetically active additives and adjuvants, or combinations of these additives, and, especially: wetting agents; depigmenting agents such as hydroquinone, azelaic acid, caffeic acid or kojic acid; emollients; moisturizing agents such as glycerol, PEG 400, thiamorpholinone and its derivatives or alternatively urea; antiseborrhoeic or antiacne agents such as S-carboxymethylcysteine, S-benzylcysteamine, salts or derivatives thereof, benzoyl peroxide; antibiotics such as erythromycin and esters thereof, neomycin, clindamycin and esters thereof, tetracyclines; antifungal agents such as ketoconazole or 4,5-polymethylene-3-isothiazolidones; agents promoting hair regrowth, such as Minoxidil (2,4-diamino-6-piperidinopyrimidine 3-oxide) and derivatives thereof, Diazoxide (7-chloro-3-methyl-1,2,4-benzothiadiazine-1,1-dioxide) and Phenytoin (5,4-diphenyl-2,4-imidazolidinedione); non-steroidal anti-inflammatory agents; carotenoids and especially β-carotene; anti-psoriatic agents such as anthralin and derivatives thereof; and, lastly, 5,8,11,14-eicosatetraynoic and 5,8,11-eicosatrynoic acids and esters and amides thereof.

The compositions according to the invention may also contain taste- or flavor-enhancing agents, preservatives such as parahydroxybenzoic acid esters, stabilizing agents, moisture regulating agents, pH regulating agents, osmotic pressure modifying agents, emulsifying agents, UV-A and UV-B screening agents, antioxidants such as α-tocopherol, butylated hydroxyanisol or butylated hydroxytoluene.

In order to further illustrate the present invention and the advantages thereof, the following specific examples are given, it being understood that same are intended only as illustrative and in nowise limitative.

EXAMPLE 1

Preparation of allyl syn-4-[α-hydroxyhexyloxyimino-(5,6,7,8-tetrahydro-5,5,8,8-tetramethyl-2-naphthyl)acetamido]benzoate

(a) Preparation of ethyl 5,6,7,8-tetrahydro-5,5,8,8-tetramethyl-2-naphthylglyoxylate 14.5 g (0.109 mol) of aluminum chloride and 100 ml of dichloromethane were introduced into a three-necked flask and a mixture of 11.7 g (62 mmol) of 5,6,7,8-tetrahydro-5,5,8,8-tetramethyl-2-naphthalene and of 8 ml (71 mmol) of ethoxalyl chloride in 100 ml of dichloromethane was added dropwise and the mixture was stirred at room temperature for one hour. The reaction medium was poured into ice, extracted with ethyl ether, the organic phase decanted off, dried over magnesium sulfate and evaporated. The residue obtained was purified by chromatography on a silica column, eluted with a mixture of dichloromethane and hexane (30/70). After evaporation of the solvents, 16.5 g (93%) of the expected ester were recovered in the form of a slightly yellow oil.

(b) Preparation of 5,6,7,8-tetrahydro-5,5,8,8-tetramethyl-2-naphthylglyoxylic acid 16 g (55.6 mmol) of ethyl 5,6,7,8-tetrahydro-5,5,8,8-tetramethyl-2-naphthylglyoxylate and 50 ml of ethyl alcohol were introduced into a round-bottomed flask. A solution of 2.5 g (58.5 mmol) of sodium hydroxide in 50 ml of water was added and the mixture was heated at reflux for one hour. The reaction medium was evaporated to dryness, taken up in water and ethyl ether, the aqueous phase decanted off, acidified to pH 1 with concentrated hydrochloric acid, extracted with ethyl ether, the organic phase decanted off, dried over magnesium sulfate and evaporated. 14 g (97%) of 5,6,7,8-tetrahydro-5,5,8,8-tetramethyl-2-naphthylglyoxylic acid were recovered in the form of a colorless oil.

(c) Preparation of 5,6,7,8-tetrahydro-5,5,8,8-tetramethyl-2-naphthylglyoxyloyl chloride 2.6 g (10 mmol) of 5,6,7,8-tetrahydro-5,5,8,8-tetramethyl-2-naphthylglyoxylic acid in 50 ml of dichloromethane were introduced into a round-bottomed flask, 2 ml (10 mmol) of dicyclohexylamine were added and the mixture was stirred at room temperature for one hour. 800 µl (10 mmol) of thionyl chloride were then added dropwise and the mixture was stirred at room temperature for one hour. The mixture was evaporated to dryness, taken up in ethyl ether, the dicyclohexylamine salt filtered and the filtrate evaporated. 2.8 g (100%) of crude acid chloride were obtained, which acid chloride was employed as is in the synthesis to follow.

(d) Preparation of allyl 4-(5,6,7,8-tetrahydro-5,5,8,8-tetramethyl-2-naphthoylcarboxamido)benzoate 3.6 g (20 mmol) of allyl 4-aminobenzoate, 2.8 ml (20 mmol) of triethylamine and 50 ml of THF were introduced into a round-bottomed flask. A solution of 5.6 g (20 mmol) of 5,6,7,8-tetrahydro-5,5,8,8-tetramethyl-2-naphthylglyoxyloyl chloride in 50 ml of THF was added dropwise and the mixture was stirred at room temperature for four hours. The reaction medium was poured into water, extracted with ethyl ether, the organic phase decanted off, dried over magnesium sulfate and evaporated. The residue obtained was purified by chromatography on a silica column, eluted with a mixture of dichloromethane and hexane (40/60). After evaporation of the solvents, 2 g (46%) of the expected allyl ester were recovered in the form of a slightly yellow oil.

(e) Preparation of allyl 4-[α-hydroxyimino-(5,6,7,8-tetrahydro-5,5,8,8-tetramethyl-2-naphthyl)acetamido]benzoate 1.7 g (4 mmol) of allyl 4-(5,6,7,8-tetrahydro-5,5,8,8-tetramethyl-2-naphthoylcarboxamido)benzoate, 1.1 g (16 mmol) of hydroxylamine hydrochloride and 50 ml of ethanol were introduced into a round-bottomed flask. 16 ml of NaOH (1N) were added dropwise and the mixture was heated at reflux for 4 hours. The reaction medium was evaporated to dryness, the residue taken up in water, extracted with ethyl ether, the organic phase decanted off, dried over magnesium sulfate and evaporated. The residue obtained was chromatographed on a silica column, eluted with a mixture of dichloromethane and ethyl ether (98/2). After evaporation of the solvents, 1.6 g (94%) of the expected compound of melting point 176°–7° C. was obtained.

(f) Synthesis of allyl syn-4-[α-hydroxyhexyloxyimino-(5,6,7,8-tetrahydro-5,5,8,8-tetramethyl-2-naphthyl)acetamido]benzoate 3.25 g (7.5 mmol) of allyl 4-[α-hydroxyimino-(5,6,7,8-tetrahydro-5,5,8,8-tetramethyl-2-naphthyl)acetamido]benzoate, 1 g (7.5 mmol) of potassium carbonate and 100 ml of methyl ethyl ketone were introduced into a round-bottomed flask. 1 ml (7.5 mmol) of 6-bromohexanol was added and the mixture was heated at reflux for 24 hours. The reaction medium was filtered, the filtrate evaporated to dryness, taken up in water and ethyl ether, the organic phase was decanted off, dried over magnesium sulfate and evaporated. The residue obtained was purified by chromatography on a silica column, eluted with dichloromethane. 3.3 g (82%) of the expected compound were thus recovered in the form of a yellow oil.

EXAMPLE 2

Preparation of syn-4-[α-hydroxyhexyloxyimino-(5,6,7,8-tetrahydro-5,5,8,8-tetramethyl-2-napthyl)acetamido]benzoic acid 3.3 g (6.2 mmol) of allyl syn-4-[α-hydroxyhexyloxyimino-(5,6,7,8-tetrahydro-5,5,8,8-tetramethyl-2-napthyl)acetamido]benzoate, 230 mg (0.2 mmol) of tetrakis(triphenylphosphine)palladium(0) and 100 ml of THF were introduced into a three-necked flask, under a nitrogen stream. 2.7 ml (31 mmol) of morpholine were then added dropwise and the mixture was stirred at room temperature for 2 hours. The reaction medium was evaporated to dryness, taken up in water, acidified to pH 1, extracted with ethyl ether, the organic phase was decanted off, washed with water, dried over magnesium sulfate and evaporated. The residue obtained was purified by chromatography on a silica column, eluted with ethyl ether and 2 g (65.5%) of syn-4-[α-hydroxyhexyloxyimino-(5,6,7,8-tetrahydro-5,5,8,8-tetramethyl-2-naphthyl)acetamido]benzoic acid of melting point 183°–6° C. were recovered.

EXAMPLE 3

Preparation of anti-4-[α-hydroxyhexyloxyimino-(5, 6,7,8-tetrahydro-5,5,8,8-tetramethyl-2-naphthyl) acetamido]benzoic acid 800 mg (1.7 mmol) of syn-4-[α-hydroxyhexyloxyimino-(5,6,7,8-tetrahydro-5,5,8,8-tetramethyl-2-naphthyl) acetamido]benzoic acid and 600 ml of methanol were introduced into a photochemical reactor and stirred for 48 hours at room temperature while irradiating (medium pressure Hanovia lamp, with no filter). The reaction medium was evaporated and the residue obtained was purified by chromatography on a silica column, eluted with a mixture of dichloromethane and methanol (98/2). After evaporation of the solvents, 470 mg (59%) of anti-4-[α-hydroxyhexyloxyimino-(5,6,7,8-tetrahydro-5,5,8,8-tetramethyl-2-naphthyl)acetamido]benzoic acid of melting point 178°–81° C. were recovered.

EXAMPLE 4

Preparation of allyl syn-4-[α-ethoxycarbonylpentyloxyimino-(5,6,7,8-tetrahydro-5,5,8,8-tetramethyl-2-naphthyl)acetamido]benzoate Following the basic procedure of Example 1 (f), 3.25 g (7.5 mmol) of allyl 4-[α-hydroxyimino(5,6,7,8-tetrahydro-5,5,8,8-tetramethyl-2-naphthyl)acetamido]benzoate were reacted with 1.3 ml (7.5 mmol) of ethyl 6-bromohexanoate. 1.7 g (39.5%) of allyl syn-4-[α-ethoxycarbonylpentyloxyimino-(5,6,7,8-tetrahydro-5,5,8,8-tetramethyl-2-naphthyl)acetamido]benzoate were obtained in the form of a slightly yellow oil.

EXAMPLE 5

Preparation of syn-4-[α-ethoxycarbonylpentyloxyimino-(5,6,7,8-tetrahydro-5,5,8,8-tetramethyl-2-naphthyl)acetamido]benzoic acid Following the basic procedure of Example 2, beginning with 1.7 g (3 mmol) of allyl syn-4-[α-methoxycarbonyl-pentyloxyimino-(5,6,7,8-tetrahydro-5,5,8,8-tetramethyl-2-naphthyl)acetamido]benzoate, 1.1 g (70%) of syn-4-[α-ethoxycarbonylpentyloxyimino-(5,6,7,8-tetrahydro-5,5,8,8-tetramethyl-2-naphthyl)acetamido]benzoic acid of melting point 152.4° C. was obtained.

EXAMPLE 6

Preparation of syn-4-[α-hydroxyoctyloxyimino-(5,6,7,8-tetrahydro-5,5,8,8-tetramethyl-2-naphthyl)acetamido]benzoic acid (a) Preparation of allyl syn-4-[α-hydroxyoctyloxyimino-(5,6,7,8-tetrahydro-5,5,8,8-tetramethyl-2-naphthyl)acetamido]benzoate Following the basic procedure of Example 1 (f), 2.2 g (5 mmol) of allyl 4-[α-hydroxyimino-(5,6,7,8-tetrahydro-5,5,8,8-tetramethyl-2-naphthyl)acetamido]benzoate were reacted with 870 µl (5 mmol) of 8-bromo-1-octanol. 2 g (70%) of the expected allyl ester were recovered in the form of a colorless oil after purification by chromatography on a silica column eluted with dichloromethane.

(b) Synthesis of syn-4-[α-hydroxyoctyloxyimino-(5, 6,7,8-tetrahydro-5,5,8,8-tetramethyl-2-naphthyl) acetamido]benzoic acid Following the basic procedure of Example 2, beginning with 2 g (3.5 mmol) of allyl syn-4-[α-hydroxyoctyloxyimino-(5,6,7,8-tetrahydro-5,5,8,8-tetramethyl-2-naphthyl)acetamido]benzoate, 1.3 g (70%) of the expected acid of melting point 102°–4° C. was obtained.

EXAMPLE 7

Preparation of trans-4-[α-hydroxyoctyloxyimino-(5, 6,7,8-tetrahydro-5,5,8,8-tetramethyl-2-naphthyl) acetamido]benzoic acid Following the basic procedure of Example 3, beginning with 900 mg (1.7 mmol) of syn-4-[α-hydroxyoctyl-oxyimino-(5,6,7,8-tetrahydro-5,5,8,8-tetramethyl-2-naphthyl)acetamido]benzoic acid, 390 mg (43%) of the expected trans acid of melting point 98°–100° C. were obtained.

EXAMPLE 8

Preparation of syn-4-[α-hydroxyheptyloxyimino-(5, 6,7,8-tetrahydro-5,5,8,8-tetramethyl-2-naphthyl) acetamido]benzoic acid (a) Preparation of allyl syn-4-[α-hydroxyheptyloxyimino-(5,6,7,8-tetrahydro-5,5,8,8-tetramethyl-2-naphthyl)acetamido]benzoate Following the basic procedure of Example 1 (f), 2.2 g (5 mmol) of allyl 4-[α-hydroxyimino-(5,6,7,8-tetrahydro-5,5, 8,8-tetramethyl-2-naphthyl)acetamido]benzoate were reacted with 780 µl (5 mmol) of 7-bromo-1-heptanol. 1.7 g (61%) of the expected allyl ester were recovered in the form of a colorless oil after purification by chromatography on a silica column, eluted with dichloromethane.

(b) Synthesis of syn-4-[α-hydroxyheptyloxyimino-(5,6,7,8-tetrahydro-5,5,8,8-tetramethyl-2-naphthyl) acetamido]benzoic acid Following the basic procedure of Example 2, beginning with 1.7 g (3.1 mmol) of allyl syn-4-[hydroxyheptyloxyimino-(5,6,7,8-tetrahydro-5,5,8,8-tetramethyl-2-naphthyl)acetamido]benzoate, 1.3 g (82%) of the expected acid of melting point 145°–55° C. was obtained.

EXAMPLE 9

Preparation of trans-4-[α-hydroxyheptyloxyimino-(5,6,7,8-tetrahydro-5,5,8,8-tetramethyl-2-naphthyl) acetamido]benzoic acid Following the basic procedure of Example 3, beginning with 900 mg (1.77 mmol) of syn-4-[α-hydroxyheptyl-oxyimino-(5,6,7,8-tetrahydro-5,5,8,8-tetramethyl-2-naphthyl)acetamido]benzoic acid, 350 mg (39%) of the expected trans acid of melting point 118°–23° C. were obtained.

EXAMPLE 10

Preparation of syn-4-[α-carboxypentyloxyimino-(5, 6,7,8-tetrahydro-5,5,8,8-tetramethyl-2-naphthyl) acetamido]benzoic acid 1.3 g (2.4 mmol) of syn-4-[α-ethoxycarbonyl-pentyloxyimino-(5,6,7,8-tetrahydro-5,5,8,8-tetramethyl-2- naphthyl)acetamido]benzoic acid and 30 ml of THF were introduced into a round-bottomed flask and 6 ml of a 2N methanolic sodium hydroxide solution were added. The mixture was stirred at room temperature for three hours, evaporated to dryness, the residue taken up in water, acidified to pH 1 with hydrochloric acid and extracted with ethyl ether. The organic phase was decanted off, dried over magnesium sulfate and evaporated. The residue obtained was purified by chromatography on a silica column, eluted with a mixture of dichloromethane and ethyl ether (95/5). After evaporation of the solvents, 1.1 g (89%) of the expected acid of melting point 162°–3° C. was recovered.

EXAMPLE 11

Preparation of trans-4-[α-hydroxypropyloxyimino-(5,6,7,8-tetrahydro-5,5,8,8-tetramethyl-2-naphthyl) acetamido]benzoic acid (a) Preparation of allyl 4-[α-hydroxypropyloxyimino-(5,6,7,8-tetrahydro-5,5,8,8-tetramethyl-2-naphthyl)acetamido]benzoate Following the basic procedure of Example 1 (f), 3.4 g (7.8 mmol) of allyl 4-[α-hydroxyimino-(5,6,7,8-tetrahydro-5,5,8,8-tetramethyl-2-naphthyl)acetamido]benzoate were reacted with 710 μl (7.8 mmol) of 3-bromo-1-propanol. 1.4 g (36%) of the syn allyl ester and 710 mg (18%) of the trans allyl ester were recovered after purification by chromatography on a silica column, eluted with dichloromethane.

(b) Synthesis of trans-4-[α-hydroxypropyloxyimino-(5,6,7,8-tetrahydro-5,5,8,8-tetramethyl-2-naphthyl)acetamido]benzoic acid Following the basic procedure of Example 2, beginning with 710 mg (1.4 mmol) of allyl trans-4-[α-hydroxypropyloxyimino-(5,6,7,8-tetrahydro-5,5,8,8-tetramethyl-2-naphthyl)acetamido]benzoate, 220 mg (35%) of the expected acid of melting point 209°–11° C. were obtained.

EXAMPLE 12

Preparation of syn-4-[α-hydroxypropyloxyimino-(5,6,7,8-tetrahydro-5,5,8,8-tetramethyl-2-naphthyl) acetamido]benzoic acid Following the basic procedure of Example 2, beginning with 1.4 g (2.8 mmol) of syn-4-[α-hydroxypropyloxyimino-(5,6,7,8-tetrahydro-5,5,8,8-tetramethyl-2-naphthyl)acetamido]benzoate, 750 mg (58%) of the expected acid of melting point 198°–204° C. were obtained.

EXAMPLE 13

Preparation of syn-4-[α-ethoxycarbonylpropyloxyimino-(5,6,7,8-tetrahydro-5,5,8,8-tetramethyl-2-naphthyl)acetamido]benzoic acid (a) Preparation of allyl syn-4-[α-ethoxycarbonylpropyloxyimino-(5,6,7,8-tetrahydro-5,5,8,8-tetramethyl-2-naphthyl)acetamido]benzoate Following the basic procedure of Example 1 (f), 4 g (9.2 mmol) of allyl 4-[α-hydroxyimino-(5,6,7,8-tetrahydro-5,5,8,8-tetramethyl-2-naphthyl)acetamido]benzoate were reacted with 1.8 g (9.2 mmol) of ethyl 4-bromobutanoate. 1.3 g (26%) of the expected allyl ester was recovered in the form of a colorless oil after purification by chromatography on a silica column, eluted with a mixture of dichloromethane and heptane (50/50%).

(b) Synthesis of syn-4-[α-ethoxycarbonylpropyloxyimino-(5,6,7,8-tetrahydro-5,5,8,8-tetramethyl-2-naphthyl)-acetamido]benzoic acid Following the basic procedure of Example 2, beginning with 1.4 g (2.5 mmol) of allyl syn-4-[α-ethoxycarbonylpropyloxyimino-(5,6,7,8)-tetrahydro-5,5,8,8-tetramethyl-2-naphthyl)acetamido]benzoate, 180 mg (14%) of the expected acid of melting point 120°–1° C. were obtained.

EXAMPLE 14

Preparation of syn-4-[α-hydroxydecyloxyimino-(5,6,7,8-tetrahydro-5,5,8,8-tetramethyl-2-naphthyl)-acetamido]benzoic acid (a) Preparation of syn-4-[α-hydroxydecyloxyimino-(5,6,7,8-tetrahydro-5,5,8,8-tetramethyl-2-naphthyl) acetamido]benzoic acid Following the basic procedure of Example 1 (f), 2.2 g (5 mmol) of allyl 4-[α-hydroxyimino-(5,6,7,8-tetrahydro-5,5,8,8-tetramethyl-2-naphthyl)-acetamido]benzoate were reacted with 995 μl (5 mmol) of 10-bromo-1-decanol. 1 g (35%) of the expected allyl ester was recovered in the form of a colorless oil after purification by chromatography on a silica column, eluted with dichloromethane.

(b) Synthesis of syn-4-[α-hydroxydecyloxyimino-(5,6,7,8-tetrahydro-5,5,8,8-tetramethyl-2-naphthyl) acetamido]benzoic acid Following the basic procedure of Example 2, beginning with 1 g (1.7 mmol) of allyl syn-4-[α-hydroxydecyloxyimino-(5,6,7,8-tetrahydro-5,5,8,8-tetramethyl-2-naphthyl)acetamido]benzoate, 400 mg (50%) of the expected acid of melting point 145°–6° C. were obtained.

EXAMPLE 15

Preparation of syn-4-[α-hydroxynonyloxyimino-(5,6,7,8-tetrahydro-5,5,8,8-tetramethyl-2-naphthyl)-acetamido]benzoic acid (a) Preparation of allyl syn-4-[α-hydroxynonyloxyimino-(5,6,7,8-tetrahydro-5,5,8,8-tetramethyl-2-naphthyl)-acetamido]benzoate Following the basic procedure of Example 1 (f), 2.2 g (5 mmol) of allyl 4-[α-hydroxyimino-(5,6,7,8-tetrahydro-5,5,8,8-tetramethyl-2-naphthyl)-acetamido]benzoate were reacted with 780 μl (5 mmol) of 7-bromo-1-heptanol. 1.7 g (61%) of the expected allyl ester was recovered in the form of a colorless oil after purification by chromatography on a silica column, eluted with dichloromethane.

(b) Synthesis of syn-4-[α-hydroxynonyloxyimino-(5,6,7,8-tetrahydro-5,5,8,8-tetramethyl-2-naphthyl) acetamido]benzoic acid Following the basic procedure of Example 2, beginning with 1.3 g (2.2 mmol) of allyl syn-4-[α-hydroxynonyloxyimino-(5,6,7,8-tetrahydro-5,5,8,8-tetramethyl-2-naphthyl)acetamido]benzoate, 600 mg (50%) of the expected acid of melting point 155°–6° C. were obtained.

EXAMPLE 16

Preparation of syn-4-[α-benzyloxyimino-(5,6,7,8-tetrahydro-5,5,8,8-tetramethyl-2-naphthyl) acetamido]benzoic acid (a) Preparation of allyl syn-4-[α-benzyloxyimino-(5,6,7,8-tetrahydro-5,5,8,8-tetramethyl-2-naphthyl) acetamido]benzoate Following the basic procedure of Example 1 (f), 2.2 g (5 mmol) of allyl 4-[α-hydroxyimino-(5,6,7,8-tetrahydro-5,5,8,8-tetramethyl-2-naphthyl)-acetamido]benzoate were reacted with 600 µl (5 mmol) of benzyl bromide. 2.6 g (98%) of the expected allyl ester were recovered in the form of a colorless oil after purification by chromatography on a silica column, eluted with a mixture of dichloromethane and heptane (60/40%).

(b) Synthesis of syn-4-[α-benzyloxyimino-(5,6,7,8-tetrahydro-5,5,8,8-tetramethyl-2-naphthyl) acetamido]benzoic acid Following the basic procedure of Example 2, beginning with 2.6 g (5 mmol) of allyl syn-4-[α-benzyloxyimino-(5,6,7,8-tetrahydro-5,5,8,8-tetramethyl-2-naphthyl)acetamido] benzoate, 1.7 g (71%) of the expected acid of melting point 223°–5° C. was obtained.

EXAMPLE 17

Preparation of syn-4-[α-methoxyethoxymethoxyimino-(5,6,7,8-tetrahydro-5,5,8,8-tetramethyl-2-naphthyl)acetamido]benzoic acid (a) Preparation of allyl syn-4-[α-methoxyethoxymethoxyimino-(5,6,7,8-tetrahydro-5,5,8,8-tetramethyl-2-naphthyl)acetamido]-benzoate Following the basic procedure of Example 1 (f), 3.3 g (7.6 mmol) of allyl 4-[α-hydroxyimino-(5,6,7,8-tetrahydro-5,5,8,8-tetramethyl-2-naphthyl)-acetamido]benzoate were reacted with 870 µl (7.6 mmol) of methoxyethoxymethane chloride. 1.2 g (30%) of the expected allyl ester was recovered in the form of a chestnut-colored oil after purification by chromatography on a silica column, eluted with a mixture of dichloromethane and heptane (70/30%).

(b) Synthesis of syn-4-[α-methoxyethoxymethoxyimino-(5,6,7,8-tetrahydro-5,5,8,8-tetramethyl-2-naphthyl)acetamido]-benzoic acid Following the basic procedure of Example 2, beginning with 1.1 g (2.1 mmol) of allyl syn-4-[α-methoxyethoxymethoxyimino-(5,6,7,8-tetrahydro-5,5,8,8-tetramethyl-2-naphthyl)acetamido]benzoate, 780 mg (77%) of the expected acid of melting point 113°–15° C. were obtained.

EXAMPLE 18

Preparation of allyl syn-4-[α-ethoxycarbonylpropylimino-(5,6,7,8-tetrahydro-5,5,8,8-tetramethyl-2-naphthyl)acetamido]benzoate Following the basic procedure of Example 1 (f), 3.9 g (9 mmol) of allyl 4-[α-hydroxyimino-(5,6,7,8-tetrahydro-5,5,8,8-tetramethyl-2-naphthyl)acetamido]benzoate were reacted with 2.8 g (9 mmol) of ethyl 8-bromooctanoate. 2.4 g (50%) of the expected allyl ester were recovered in the form of a colorless oil after purification by chromatography on a silica column, eluted with dichloromethane.

EXAMPLE 19

Preparation of (Z)-4-[2-(5,6,7,8-tetrahydro-5,5,8,8-tetramethyl-2-naphthyl)-2-nonenamido]benzoic acid (a) Preparation of 2-(5,6,7,8-tetrahydro-5,5,8,8-tetramethyl-2-naphthyl)-2-nonenoic acid 1 g (3.8 mmol) of 5,6,7,8-tetrahydro-5,5,8,8-tetramethyl-2-naphthylglyoxylic acid and 10 ml of DMSO were introduced into a three-necked flask under a nitrogen stream. 2.37 ml of n-BuLi (1.6 M in hexane) were added dropwise and the mixture was stirred at room temperature for 15 minutes. 2 g (4.5 mmol) of n-heptyltriphenylphosphine bromide were then added and 2.85 ml (4.5 mmol) of n-BuLi (1.6 M in hexane) were added dropwise and the mixture was stirred at room temperature for one hour. The reaction medium was poured into water, adjusted to pH 1 with hydrochloric acid, extracted with ethyl ether, the organic phase decanted off, dried over magnesium sulfate and evaporated. The residue obtained was purified by chromatography on a silica column, eluted with a mixture of ethyl ether and heptane (40/60). 380 mg (28%) of the expected compound were recovered in the form of an oil after evaporation of the solvents.

(b) Preparation of 2-(5,6,7,8-tetrahydro-5,5,8,8-tetramethyl-2-naphthyl)-2-nonenoyl chloride 1.7 g (5 mmol) of 2-(5,6,7,8-tetrahydro-5,5,8,8-tetramethyl-2-naphthyl)-2-nonenoic acid, 20 ml of toluene and 73 µl of DMF were introduced into a round-bottomed flask. The mixture was heated to 50° C. and 714 µl (6 mmol) of thionyl chloride were added and the mixture was stirred at this temperature for one hour. The mixture was evaporated to dryness and the crude acid chloride was employed as is in the synthesis to follow.

(c) Preparation of methyl (Z)- and (E)-4-[2-(5,6,7,8-tetrahydro-5,5,8,8-tetramethyl-2-naphthyl)-2-nonenamido]benzoate 830 mg (5.5 mmol) of methyl 4-aminobenzoate, 20 ml of THF and 612 µl (6 mmol) of triethylamine were introduced into a three-necked flask under a nitrogen stream. The acid chloride prepared above, dissolved in 10 ml of THF, was added dropwise and the mixture was stirred at room temperature for eight hours. The reaction medium was poured into water, extracted with ethyl ether, the organic phase decanted off, dried over magnesium sulfate and evaporated. A mixture of the two geometric isomers was recovered, which isomers were separated by chromatography on a silica column, eluted with a mixture of dichloromethane and heptane (65/35). The following compounds were recovered:

(i) 1 g (42%) of methyl (Z)-4-[2-(5,6,7,8-tetrahydro-5,5,8,8-tetramethyl-2-naphthyl)-2-nonenamido]benzoate of melting point 129°–30° C.

(ii) 400 mg (18%) of methyl (E)-4-[2-(5,6,7,8-tetrahydro-5,5,8,8-tetramethyl-2-naphthyl)-2-nonenamido]benzoate of melting point 86°–7° C.

(d) Synthesis of (Z)-4-[2-(5,6,7,8-tetrahydro-5,5,8,8-tetramethyl-2-naphthyl)-2-nonenamido]benzoic acid 700 mg (1.47 mmol) of methyl (Z)-4-[2-(5,6,7,8-tetrahydro-5,5,8,8-tetramethyl-2-naphthyl)-2-nonenamido]

benzoate, 25 ml of methanol and 1.2 ml (14.7 mmol) of a 35% sodium hydroxide solution were introduced into a round-bottomed flask. The mixture was stirred at room temperature for 12 hours, the reaction medium was poured into water, acidified to pH 1 with hydrochloric acid (37%), extracted with ethyl ether, the organic phase decanted off, dried over magnesium sulfate and evaporated. The residue was triturated in heptane, filtered and dried. 555 mg (82%) of (Z)-4-[2-(5,6,7,8-tetrahydro-5,5,8,8-tetramethyl-2-naphthyl)-2-nonenamido]benzoic acid of melting point 183°–4° C. were recovered.

EXAMPLE 20

Preparation of (E)-4-[2-(5,6,7,8-tetrahydro-5,5,8,8-tetramethyl-2-naphthyl)-2-hexadecenamido]benzoic acid (a) Preparation of 2-(5,6,7,8-tetrahydro-5,5,8,8-tetramethyl-2-naphthyl)-2-hexadecenoic acid Following the basic procedure of Example 19 (a), 9.65 g (37.1 mmol) of 5,6,7,8-tetrahydro-5,5,8,8-tetramethyl-2-naphthylglyoxlic acid were reacted with 24 g (44.5 mmol) of tetradecyltriphenylphosphine bromide. 4.53 g (28%) of the expected compound of melting point 59°–60° C. were obtained in the form of an oil which crystallized slowly after purification on a silica column, eluted with dichloromethane.

(b) Preparation of 2-(5,6,7,8-tetrahydro-5,5,8,8-tetramethyl-2-naphthyl)-2-hexadecenonyl chloride Following the basic procedure of Example 19 (b), 2 g (4.5 mmol) of 2-(5,6,7,8-tetrahydro-5,5,8,8-tetramethyl-2-naphthyl)-2-hexadecenoic acid were reacted with 648 µl (5.4 mmol) of thionyl chloride. The acid chloride obtained was employed as is, in the crude form, in the synthesis to follow.

(c) Preparation of methyl (Z)-4-[2-(5,6,7,8-tetrahydro-5,5,8,8-tetramethyl-2-naphthyl)-2-hexadecenamido]benzoate Following the basic procedure of Example 19 (c), the acid chloride obtained above was reacted with 755 mg (5 mmol) of methyl 4-aminobenzoate. 1.16 g (42%) of methyl (Z)-4-[2-(5,6,7,8-tetrahydro-5,5,8,8-tetramethyl-2-naphthyl)-2-hexadecenamido]benzoate of melting point 93°–4° C. was obtained after chromatography on a silica column, eluted with a mixture of dichloromethane and heptane (50/50).

(d) Synthesis of (Z)-4-[2-(5,6,7,8-tetrahydro-5,5,8,8-tetramethyl-2-naphthyl)-2-hexadecenamido]benzoic acid Following the basic procedure of Example 19 (d), beginning with 503 mg (0.9 mmol) of methyl (Z)-4-[2-(5,6,7,8-tetrahydro-5,5,8,8-tetramethyl-2-naphthyl)-2-hexadecenamido]benzoate, 435 mg (89%) of (Z)-4-[2-(5,6,7,8-tetrahydro-5,5,8,8-tetramethyl-2-naphthyl)-2-hexadecenamido]benzoic acid of melting point 164°–5° C. were obtained.

EXAMPLE 21

In this example, various specific formulations based on the compounds according to the invention are illustrated.

(A) Oral Route (a) 0.2 g Tablet:

| | |
|---|---|
| (i) Compound prepared in Example 3 | 0.001 g |
| (ii) Starch | 0.114 g |
| (iii) Dicalcium phosphate | 0.020 g |
| (iv) Silica | 0.020 g |
| (v) Lactose | 0.030 g |
| (vi) Talc | 0.010 g |
| (vii) Magnesium stearate | 0.005 g |

(b) Oral suspension in 5 ml ampoules:

| | |
|---|---|
| (i) Compound prepared in Example 4 | 0.001 g |
| (ii) Glycerine | 0.500 g |
| (iii) Sorbitol at 70% | 0.500 g |
| (iv) Sodium saccharinate | 0.010 g |
| (v) Methyl parahydroxybenzoate | 0.040 g |
| (vi) Flavoring | qs |
| (vii) Purified water | qs 5 ml |

(B) Topical Route (a) Ointment:

| | |
|---|---|
| (i) Compound of Example 3 | 0.020 g |
| (ii) Isopropyl myristate | 81.700 g |
| (iii) Fluid paraffin oil | 9.100 g |
| (iv) Silica ("Aerosil 200" marketed by DEGUSSA) | 9.180 g |

(b) Ointment:

| | |
|---|---|
| (i) Compound of Example 5 | 0.300 g |
| (ii) Petroleum jelly | 100 g |

(c) Non-ionic water-in-oil cream:

| | |
|---|---|
| (i) Compound of Example 4 | 0.100 g |
| (ii) Mixture of emulsive lanolin alcohols, waxes and oils ("anhydrous Eucerin" marketed by BDF) | 39.900 g |
| (iii) Methyl parahydroxybenzoate | 0.075 g |
| (iv) Propyl parahydroxybenzoate | 0.075 g |
| (v) Sterile demineralized water | qs 100 g |

(d) Lotion:

| | |
|---|---|
| (i) Compound of Example 5 | 0.100 g |
| (ii) Polyethylene glycol (PEG 400) | 69.900 g |
| (iii) Ethanol at 95% | 30.000 g |

(e) Hydrophobic ointment:

| | |
|---|---|
| (i) Compound of Example 2 | 0.300 g |
| (ii) Isopropyl myristate | 36.400 g |
| (iii) Silicone oil ("Rhodorsil 47 V 300" marketed by RHONE-POULENC) | 36.400 g |

| | |
|---|---|
| (iv) Beeswax | 13,600 g |
| (v) Silicone oil ("Abil 300.000 cst" marketed by GOLDSCHMIDT) | 100 g |

(f) Non-ionic oil-in-water cream:

| | |
|---|---|
| (i) Compound of Example 3 | 1.000 g |
| (ii) Cetyl alcohol | 4.000 g |
| (iii) Glycerol monostearate | 2.500 g |
| (iv) PEG 50 stearate | 2.500 g |
| (v) Shea butter | 9.200 g |
| (vi) Propylene glycol | 2.000 g |
| (vii) Methyl parahydroxybenzoate | 0.075 g |
| (viii) Propyl parahydroxybenzoate | 0.075 g |
| (ix) Sterile demineralized water | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method of treating a condition selected from the group consisting of a keratinization disorder, a dermatological disorder, an ophthalmological disorder, skin aging, epidermal and/or dermal atrophy, a cicatrization disorder, auspicious function disorder, a cancerous or precancerous disease state, an inflammatory disorder, viral infection, a cardiovascular disorder, seasonally related depression, immune deficiency, by administering a therapeutically effective amount of a biaromatic amido compound having the structural formula (I):

(I)

in which Ar is a radical (a):

(a)

in which $R_5$ and $R_6$ are as defined below; Z is —CO—$NR_7$—; $R_1$ is (i) a —$CH_3$ radical, (ii) a radical —$CH_2$—O—$R_6$, (iii) a radical —O—$R_6$, (iv) a radical —CO—$R_8$ or (v) a radical —S(O)$_t$$R_9$, wherein $R_6$, $R_8$, $R_9$ and t are as defined below; X and Y may be taken separately, in which event X is a hydrogen atom or a lower alkyl radical, and Y is a radical of the formula —(CH$_2$)$_n$—CH$_3$ or of the formula —(CH$_2$)$_n$—$R_{10}$, or X and Y may be taken together, in which event X and Y together form, with the carbon atom from which they depend, a single radical containing a double bond, selected from among those of the formulae =N—O—(CH$_2$)$_n$—$R_{10}$, =CH—(CH$_2$)$_m$—$R_{10}$, =N—O—(CH$_2$)$_2$—O—CH$_2$—CH$_3$, =N—O—CH$_2$—O—CH$_2$—CH$_2$—O—CH$_3$ and =CH—(CH$_2$)$_m$—CH$_3$, wherein $R_{10}$, m and n are as defined below; $R_2$ and $R_3$, taken separately, are each a hydrogen atom, a linear or branched alkyl radical having from 1 to 20 carbon atoms, a radical —OR$_6$ or a radical —SR$_6$, wherein $R_6$ is as defined below, with the proviso that $R_2$ and $R_3$ cannot simultaneously be a hydrogen atom, a radical —OR$_6$ or a radical —SR$_6$, or $R_2$ and $R_3$ together form, with the adjacent aromatic ring from which they depend, a 5- or 6-membered ring optionally substituted by methyl radicals and/or optionally interrupted by an oxygen or sulfur atom or by an —SO— or —SO$_2$— radical; $R_4$ is a hydrogen atom, a halogen atom, a lower alkyl radical or a radical —OR$_6$, wherein $R_6$ is as defined below, with the proviso that $R_5$ has the same definition as $R_4$; $R_6$ is a hydrogen atom, a linear or branched alkyl radical having from 1 to 20 carbon atoms or a radical —CO—$R_{11}$, wherein $R_{11}$ is as defined below; $R_7$ is a hydrogen atom or a lower alkyl radical; $R_8$ is (a) a hydrogen atom, (b) a lower alkyl radical, (c) a radical of the formula:

wherein R' and R" are as defined below, or (d) a radical —OR$_{12}$, wherein $R_{12}$ is as defined below; $R_9$ and $R_{11}$, which may be identical or different, are each a lower alkyl radical; $R_{10}$ is (i) a radical —OR$_6$, (ii) a radical —CO—$R_8$, (iii) a radical of the formula:

wherein R' and R" are as defined below, (iv) an optionally substituted aryl radical, (v) a heterocyclic radical, or (vi) a $C_3$ or $C_6$ cycloaliphatic radical; $R_{12}$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; R' and R", which may be identical or different, are each a hydrogen atom, a lower alkyl radical, a mono- or polyhydroxyalkyl radical, an optionally substituted aryl radical or an amino acid or peptide or sugar residue, with the proviso that R' and R" may together form, with the nitrogen atom from which they depend, a heterocycle; m is an integer ranging from 1 to 20; n is an integer ranging from 2 to 20; and t is an integer equal to 0, 1 or 2; or a pharmaceutically/cosmetically salt or geometric or optical isomer thereof, wherein said compound is comprised in a dermatologically or pharmaceutically acceptable carrier.

2. A method for treating or preventing alopecia in a mammalian organism in need of such treatment, comprising administering to such organism a therapeutically effective amount of a pharmaceutically composition comprising a therapeutically effective amount of at least one biaromatic amido compound having the structural formula (I):

(I)

in which Ar is a radical (a):

(a)

in which $R_5$ and $R_6$ are as defined below; Z is —CO—$NR_7$—; $R_1$ is (i) a —$CH_3$ radical, (ii) a radical —$CH_2$—O—$R_6$, (iii) a radical —O—$R_6$, (iv) a radical —CO—$R_8$ or (v) a radical —S(O)$_t$R$_9$, wherein $R_6$, $R_8$, $R_9$ and t are as defined below; X and Y may be taken separately, in which event X is a hydrogen atom or a lower alkyl radical, and Y is a radical of the formula —(CH$_2$)$_n$—CH$_3$ or of the formula —(CH$_2$)$_n$—R$_{10}$, or X and Y may be taken together, in which event X and Y together form, with the carbon atom from which they depend, a single radical containing a double bond, selected from among those of the formulae =N—O—(CH$_2$)$_n$—R$_{10}$, =CH—(CH$_2$)$_m$—R$_{10}$, =N—O—(CH$_2$)$_2$—O—CH$_2$—CH$_3$, =N—O—CH$_2$—O—CH$_2$—CH$_2$—O—CH$_3$ and =CH—(CH$_2$)$_m$—CH$_3$, wherein $R_{10}$, m and n are as defined below; $R_2$ and $R_3$, taken separately, are each a hydrogen atom, a linear or branched alkyl radical having from 1 to 20 carbon atoms, a radical —OR$_6$ or a radical —SR$_6$, wherein $R_6$ is as defined below, with the proviso that $R_2$ and $R_3$ cannot simultaneously be a hydrogen atom, a radical —OR6 or a radical —SR$_6$, or $R_2$ and $R_3$ together form, with the adjacent aromatic ring from which they depend, a 5- or 6-membered ring optionally substituted by methyl radicals and/or optionally interrupted by an oxygen or sulfur atom or by an —SO— or —SO$_2$— radical; $R_4$ is a hydrogen atom, a halogen atom, a lower alkyl radical or a radical —OR$_6$, wherein $R_6$ is as defined below, with the proviso that $R_5$ has the same definition as $R_4$; $R_6$ is a hydrogen atom, a linear or branched alkyl radical having from 1 to 20 carbon atoms or a radical —CO—R$_{11}$, wherein $R_{11}$ is as defined below; $R_7$ is a hydrogen atom or a lower alkyl radical; $R_8$ is (a) a hydrogen atom, (b) a lower alkyl radical, (c) a radical of the formula:

wherein R' and R" are as defined below, or (d) a radical —OR$_{12}$, wherein $R_{12}$ is as defined below; $R_9$ and $R_{11}$, which may be identical or different, are each a lower alkyl radical; $R_{10}$ is (i) a radical —OR$_6$, (ii) a radical —CO—R$_8$, (iii) a radical of the formula:

wherein R' and R" are as defined below, (iv) an optionally substituted aryl radical, (v) a heterocyclic radical, or (vi) a $C_3$ or $C_6$ cycloaliphatic radical; $R_{12}$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; R' and R", which may be identical or different, are each a hydrogen atom, a lower alkyl radical, a mono- or polyhydroxyalkyl radical, an optionally substituted aryl radical or an amino acid or peptide or sugar residue, with the proviso that R' and R" may together form, with the nitrogen atom from which they depend, a heterocycle; m is an integer ranging from 1 to 20; n is an integer ranging from 2 to 20; and t is an integer equal to 0, 1 or 2; or a pharmaceutically/cosmetically salt or geometric or optical isomer thereof.

3. A method of treating or preventing osteoporosis in a mammalian organism in need of such treatment, comprising administering to such organism a therapeutically effective amount of a pharmaceutical composition comprising a biaromatic amide compound having the following structure:

(I)

in which Ar is a radical (a):

(a)

in which $R_5$ and $R_6$ are as defined below; Z is —CO—$NR_7$—; $R_1$ is (i) a —$CH_3$ radical, (ii) a radical —$CH_2$—O—$R_6$, (iii) a radical —O—$R_6$, (iv) a radical —CO—$R_8$ or (v) a radical —S(O)$_t$R$_9$, wherein $R_6$, $R_8$, $R_9$ and t are as defined below; X and Y may be taken separately, in which event X is a hydrogen atom or a lower alkyl radical, and Y is a radical of the formula —(CH$_2$)$_n$—CH$_3$ or of the formula —(CH$_2$)$_n$—R$_{10}$, or X and Y may be taken together, in which event X and Y together form, with the carbon atom from which they depend, a single radical containing a double bond, selected from among those of the formulae =N—O—(CH$_2$)$_n$—R$_{10}$, =CH—(CH$_2$)$_m$—R$_{10}$,=N—O—(CH$_2$)$_2$—O—CH$_2$—CH$_3$, =N—O—CH$_2$—O—CH$_2$—CH$_2$—O—CH$_3$ and =CH—(CH$_2$)$_m$—CH$_3$, wherein $R_{10}$, m and n are as defined below; $R_2$ and $R_3$, taken separately, are each a hydrogen atom, a linear or branched alkyl radical having from 1 to 20 carbon atoms, a radical —OR$_6$ or a radical —SR$_6$, wherein $R_6$ is as defined below, with the proviso that $R_2$ and $R_3$ cannot simultaneously be a hydrogen atom, a radical —OR$_6$ or a radical —SR$_6$, or $R_2$ and $R_3$ together form, with the adjacent aromatic ring from which they depend, a 5- or 6-membered ring optionally substituted by methyl radicals and/or optionally interrupted by an oxygen or sulfur atom or by an —SO— or —SO$_2$— radical; R$_4$ is a hydrogen atom, a halogen atom, a lower alkyl radical or a radical —OR$_6$, wherein R$_6$ is as defined below, with the proviso that R$_5$ has the same definition as R$_4$; R$_6$ is a hydrogen atom, a linear or branched alkyl radical having from 1 to 20 carbon atoms or a radical —CO—R$_{11}$, wherein R$_{11}$ is as defined below; R$_7$ is a hydrogen atom or a lower alkyl radical; R$_8$ is (a) a hydrogen atom, (b) a lower alkyl radical, (c) a radical of the formula:

wherein R' and R" are as defined below, or (d) a radical —OR$_{12}$, wherein R$_{12}$ is as defined below; R$_9$ and R$_{11}$, which may be identical or different, are each a lower alkyl radical; R$_{10}$ is (i) a radical —OR$_6$, (ii) a radical —CO—R$_8$, (iii) a radical of the formula:

wherein R' and R" are as defined below, (iv) an optionally substituted aryl radical, (v) a heterocyclic radical, or (vi) a C$_3$ or C$_6$ cycloaliphatic radical; R$_{12}$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; R' and R", which may be identical or different, are each a hydrogen atom, a lower alkyl radical, a mono- or polyhydroxyalkyl radical, an optionally substituted aryl radical or an amino acid or peptide or sugar residue, with the proviso that R' and R" may together form, with the nitrogen atom from which they depend, a heterocycle; m is an integer ranging from 1 to 20; n is an integer ranging from 2 to 20; and t is an integer equal to 0, 1 or 2; or a pharmaceutically/cosmetically salt or geometric or optical isomer thereof, wherein said compound is comprised in a dermatologically or pharmaceutically acceptable carrier.

4. The method of claim 1, wherein the daily dosage of said biaromatic amido compound ranges from about 0.01 mg/kg to 100 mg/kg of body weight thereof.

5. The method of claim 2, wherein the daily dosage of said biaromatic amido compound ranges from about 0.01 mg/kg to 100 mg/kg of body weight thereof.

6. The method of claim 3, wherein the daily dosage of said biaromatic amido compound ranges from about 0.01 mg/kg to 100 mg/kg of body weight thereof.

7. A method of treating a skin or hair disorder in a mammalian organism in need of such treatment, comprising administering to such organism a cosmetically/dermatologically effective amount of a cosmetic composition comprising a cosmetically effective amount of at least one biaromatic amide compound having the following structure:

in which Ar is a radical (a):

in which R$_5$ and R$_6$ are as defined below; Z is —CO—NR$_7$—; R$_1$ is (i) a —CH$_3$ radical, (ii) a radical —CH$_2$—O—R$_6$, (iii) a radical —O—R$_6$, (iv) a radical —CO—R$_8$ or (v) a radical —S(O)$_t$R$_9$, wherein R$_6$, R$_8$, R$_9$ and t are as defined below; X and Y may be taken separately, in which event X is a hydrogen atom or a lower alkyl radical, and Y is a radical of the formula —(CH$_2$)$_n$—CH$_3$ or of the formula —(CH$_2$)$_n$—R$_{10}$, or X and Y may be taken together, in which event X and Y together form, with the carbon atom from which they depend, a single radical containing a double bond, selected from among those of the formulae =N—O—(CH$_2$)$_n$—R$_{10}$, =CH—(CH$_2$)$_m$—R$_{10}$, =N—O—(CH$_2$)$_2$—O—CH$_2$—CH$_3$, =N—O—CH$_2$—O—CH$_2$—CH$_2$—O—CH$_3$ and =CH—(CH$_2$)$_m$—CH$_3$, wherein R$_{10}$, m and n are as defined below; R$_2$ and R$_3$, taken separately, are each a hydrogen atom, a linear or branched alkyl radical having from 1 to 20 carbon atoms, a radical —OR$_6$ or a radical —SR$_6$, wherein R$_6$ is as defined below, with the proviso that R$_2$ and R$_3$ cannot simultaneously be a hydrogen atom, a radical —OR$_6$ or a radical —SR$_6$, or R$_2$ and R$_3$ together form, with the adjacent aromatic ring from which they depend, a 5- or 6-membered ring optionally substituted by methyl radicals and/or optionally interrupted by an oxygen or sulfur atom or by an —SO— or —SO$_2$— radical; R$_4$ is a hydrogen atom, a halogen atom, a lower alkyl radical or a radical —OR$_6$, wherein R$_6$ is as defined below, with the proviso that R$_5$ has the same definition as R$_4$; R$_6$ is a hydrogen atom, a linear or branched alkyl radical having from 1 to 20 carbon atoms or a radical —CO—R$_{11}$, wherein R$_{11}$ is as defined below; R$_7$ is a hydrogen atom or a lower alkyl radical; R$_8$ is (a) a hydrogen atom, (b) a lower alkyl radical, (c) a radical of the formula:

wherein R' and R" are as defined below, or (d) a radical —OR$_{12}$, wherein R$_{12}$ is as defined below; R$_9$ and R$_{11}$, which may be identical or different, are each a lower alkyl radical; R$_{10}$ is (i) a radical —OR$_6$, (ii) a radical —CO—R$_8$, (iii) a radical of the formula:

wherein R' and R" are as defined below, (iv) an optionally substituted aryl radical, (v) a heterocyclic radical, or (vi) a $C_3$ or $C_6$ cycloaliphatic radical; $R_{12}$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; R' and R", which may be identical or different, are each a hydrogen atom, a lower alkyl radical, a mono- or polyhydroxyalkyl radical, an optionally substituted aryl radical or an amino acid or peptide or sugar residue, with the proviso that R' and R" may together form, with the nitrogen atom from which they depend, a heterocycle; m is an integer ranging from 1 to 20; n is an integer ranging from 2 to 20; and t is an integer equal to 0, 1 or 2; or a pharmaceutically/cosmetically salt or geometric or optical isomer thereof, wherein said compound is comprised in a dermatologically or pharmaceutically acceptable carrier.

8. The method of claim 7, wherein said cosmetic composition further comprises at least one substituent selected from the group consisting of a wetting agent, depigmenting agent, moisturizing agent, anti-seborrhoeic or anti-acne agent, antibiotic, anti-fungal agent, hair regrowth promoter, non-steroidal anti-inflammatory agent, carotenoid, anti-psoriatic agent, 5,8,11,14-eicosatetraynoic or 5,8,11-eicosatrynoic acid or ester or amide thereof, and combinations thereof.

9. The method of claim 8, wherein the administered cosmetic composition further comprises another agent selected from the group consisting of a taste or flavor-enhancing agent, preservative, stabilizer, moisture regulating agent, pH regulating agent, osmotic pressure modifying agent, emulsifying agent, UV-A or UV-B screening agent, antioxidant, and combinations thereof.

10. The method of claim 1, wherein the administered pharmaceutical composition comprises from 0.001% to 5% by weight of said biaromatic amid compound, or salt or isomer thereof.

11. The method of claim 2, wherein the administered pharmaceutical composition comprises from 0.001% to 5% by weight of said biaromatic amido compound, or salt or isomer thereof.

12. The method of claim 3, wherein the administered pharmaceutical composition comprises from 0.001% to 5% by weight of said biaromatic amido compound, or salt or isomer thereof.

13. The method of claim 1, wherein said compound is administered in a form selected from the group consisting of a tablet, capsule, syrup, suspension, elixir, solution, powder, granules, emulsion, microspheres, nanospheres, lipid vesicles, polymeric vesicles, and an injectable composition.

14. The method of claim 1, wherein said compound is administered in a form selected from the group consisting of an ointment, cream, milk, pommade, impregnated pad, gel, spray and a lotion.

15. The method of claim 1, wherein the compound is administered topically.

16. The method of claim 1, wherein said compound is administered systemically.

17. The method of claim 1, wherein said compound is administered in combination with another compound selected from the group consisting of a retinoid compound, vitamin D or derivative thereof, a corticoid steroid, anti-free radical agent, α-hydroxy or α-keto acid or derivative thereof, ion channel blocker, and combinations thereof.

18. The method of claim 1, wherein said biaromatic amido compound is selected from the group consisting of anti-4-[α-hydroxyhexylimino-(5,6,7,8-tetrahydro-5,5,8,8-tetramethyl-2-naphthyl)acetamido]benzoic acid; syn-4-[α-hydroxyhexylimino-(5,6,7,8-tetrahydro-5,5,8,8-tetramethyl-2-naphthyl)acetamido]benzoic acid; syn-4-[α-methoxycarbonylpentylimino-(5,6,7,8-tetrahydro-5,5,8,8-tetramethyl-2naphthyl)-acetamido]benzoic acid; syn-4-[α-hydroxyoctyloxyimino-(5,6,7,8-tetrahydro-5,5,8,8-tetramethyl-2-naphthyl)acetamido]benzoic acid; trans-4-[α-hydroxyoctyloxyimino-(5,6,7,8-tetrahydro-5,5,8,8-tetramethyl-2-naphthyl)acetamido]benzoic acid; syn-4-[α-hydroxyheptyloxyimino-(5,6,7,8-tetrahydro-5,5,8,8-tetramethyl-2-naphthyl)acetamido]-benzoicacid;trans-4-[α-hydroxyheptyloxyimino-(5,6,7,8-tetrahydro-5,5,8,8-tetramethyl-2-naphthyl)acetamido]benzoic acid; syn-4-[α-hydroxypropyloxyimino-(5,6,7,8-tetrahydro-5,5,8,8-tetramethyl-2-naphthyl)acetamido]benzoic acid; trans-4-[α-hydroxypropyloxyimino-(5,6,7,8-tetrahydro-5,5,8,8-tetramethyl-2-naphthyl)acetamido]benzoic acid; syn-4-[α-ethoxycarbonylpropyloxyimino-(5,6,7,8-tetrahydro-5,5,8,8-tetramethyl-2-naphthyl)acetamido]benzoic acid; syn-4-[α-hydroxydecyloxyimino-(5,6,7,8-tetrahydro-5,5,8,8-tetramethyl-2-naphthyl)acetamido]benzoic acid; syn-4-[α-hydroxynonyloxyimino-(5,6,7,8-tetrahydro-5,5,8,8-tetramethyl-2-naphthyl)acetamido]benzoic acid; syn-4-[α-benzyloxyimino-(5,6,7,8-tetrahydro-5,5,8,8-tetramethyl-2-naphthyl)acetamido]benzoic acid; syn-4-[α-methoxyethoxymethoxyimino-(5,6,7,8-tetrahydro-5,5,8,8-tetramethyl-2-naphthyl)acetamido]benzoic acid; allyl syn-4-[α-ethoxycarbonylpropyloxyimino-(5,6,7,8-tetrahydro-5,5,8,8-tetramethyl-2-naphthyl)acetamido]benzoate; (E)-4-[2-(5,6,7,8-tetrahydro-5,5,8,8-tetramethyl-2-naphthyl)-2-nonenamido]benzoic acid; (Z)-4-[2-(5,6,7,8-tetrahydro-5,5,8,8-tetramethyl-2-naphthyl)-2-nonenamido]benzoic acid; (E)-4-[2-(5,6,7,8-tetrahydro-5,5,8,8-tetramethyl-2-naphthyl)-2-undecenamido]benzoic acid; (E)-4-[2-(5,6,7,8-tetrahydro-5,5,8,8-tetramethyl-2-naphthyl)-2-undecenamido]phenylcarboxamide; (E)-4-[2-(5,6,7,8-tetrahydro-5,5,8,8-tetramethyl-2-naphthyl)-2-undecenamido]-benzenemethanol; (E)-4-[2-(5,6,7,8-tetrahydro-5,5,8,8-tetramethyl-2-naphthyl)-2-undecenamido]phenol; (Z)-4-[2-(5,6,7,8-tetrahydro-5,5,8,8-tetramethyl-2-naphthyl)-2-undecenamido]benzoic acid; (E)-4-[2-(5,6,7,8-tetrahydro-5,5,8,8-tetramethyl-2-naphthyl)-2-hexadecenamido]benzoic acid; and (Z)-4-[2-(5,6,7,8-tetrahydro-5,5,8,8-tetramethyl-2-naphthyl)-2-hexadecenamido]benzoic acid.

19. The method of claim 2, wherein said biaromatic amido compound is selected from the group consisting of anti-4-[α-hydroxyhexylimino-(5,6,7,8-tetrahydro-5,5,8,8-tetramethyl-2-naphthyl)acetamido]benzoic acid; syn-4-[α-hydroxyhexylimino-(5,6,7,8-tetrahydro-5,5,8,8-tetramethyl-2-naphthyl)acetamido]benzoic acid; syn-4-[α-methoxycarbonylpentylimino-(5,6,7,8-tetrahydro-5,5,8,8-tetramethyl-2-naphthyl)-acetamido]benzoic acid; syn-4-[α-hydroxyoctyloxyimino-(5,6,7,8-tetrahydro-5,5,8,8-tetramethyl-2-naphthyl)acetamido]benzoic acid; trans-4-[α-hydroxyoctyloxyimino-(5,6,7,8-tetrahydro-5,5,8,8-tetramethyl-2-naphthyl)acetamido]benzoic acid; syn-4-[α-hydroxyheptyloxyimino-(5,6,7,8-tetrahydro-5,5,8,8-tetramethyl-2-naphthyl)acetamido]-benzoicacid;trans-4-[α-hydroxyheptyloxyimino-(5,6,7,8-tetrahydro-5,5,8,8-tetramethyl-2-naphthyl)acetamido]benzoic acid; syn-4-[α- hydroxypropyloxyimino-(5,6,7,8-tetrahydro-5,5,8,8-tetramethyl-2-naphthyl)acetamido]benzoic acid; trans-4-[α-hydroxy-propyloxyimino-(5,6,7,8-tetrahydro-5,5,8,8-tetramethyl-2-naphthyl)acetamido]benzoic acid; syn-4-[α-ethoxycarbonylpropyloxyimino-(5,6,7,8-tetrahydro-5,5,8,8-tetramethyl-2-naphthyl)acetamido]benzoic acid; syn-4-[α-hydroxydecyloxyimino-(5,6,7,8-tetrahydro-5,5,8,8-tetramethyl-2-naphthy)acetamido]benzoic acid; syn-4-[α-hydroxynonyloxyimino-(5,6,7,8-tetrahydro-5,5,8,8-tetramethyl-2-naphthyl)acetamido]benzoic acid; syn-4-[α-benzyloxyimino-(5,6,7,8-tetrahydro-5,5,8,8-tetramethyl-2-naphthyl)acetamido]benzoic acid; syn-4-[α-methoxyethoxymethoxyimino-(5,6,7,8-tetrahydro-5,5,8,8-tetramethyl-2-naphthyl)acetamido]benzoic acid; allyl syn-4-[α-ethoxycarbonylpropyloxyimino-(5,6,7,8-tetrahydro-5,5,8,8-tetramethyl-2-naphthyl)acetamido]benzoate; (E)-4-[2-(5,6,7,8-tetrahydro-5,5,8,8-tetramethyl-2-naphthyl)-2-nonenamido]benzoic acid; (Z)-4-[2-(5,6,7,8-tetrahydro-5,5,8,8-tetramethyl-2-naphthyl)-2-nonenamido]benzoic acid; (E)-4-[2-(5,6,7,8-tetrahydro-5,5,8,8-tetramethyl-2-naphthyl)-2-undecenamido]benzoic acid; (E)-4-[2-(5,6,7,8-tetrahydro-5,5,8,8-tetramethyl-2-naphthyl)-2-undecenamido]phenylcarboxamide; (E)-4-[2-(5,6,7,8-tetrahydro-5,5,8,8-tetramethyl-2-naphthyl)-2-undecenamido]-benzenemethanol; (E)-4-[2-(5,6,7,8-tetrahydro-5,5,8,8-tetramethyl-2-naphthyl)-2-undecenamido]phenol; (Z)-4-[2-(5,6,7,8-tetrahydro-5,5,8,8-tetramethyl-2-naphthyl)-2-undecenamido]benzoic acid; (E)-4-[2-(5,6,7,8-tetrahydro-5,5,8,8-tetramethyl-2-naphthyl)-2-hexadecenamido]benzoic acid; and (Z)-4-[2-(5,6,7,8-tetrahydro-5,5,8,8-tetramethyl-2-naphthyl)-2-hexadecenamido]benzoic acid.

20. The method of claim 3, wherein said biaromatic amido compound is selected from the group consisting of anti-4-[α-hydroxyhexylimino-(5,6,7,8-tetrahydro-5,5,8,8-tetramethyl-2-naphthyl)acetamido]benzoic acid; syn-4-[α-hydroxyhexylimino-(5,6,7,8-tetrahydro-5,5,8,8-tetramethyl-2-naphthyl)acetamido]benzoic acid; syn-4-[α-methoxycarbonylpentylimino-(5,6,7,8-tetrahydro-5,5,8,8-tetrahydro-2-naphthyl)-acetamido]benzoic acid; syn-4-[α-hydroxyoctyloxyimino-(5,6,7,8-tetrahydro-5,5,8,8-tetramethyl-2-naphthyl)acetamido]benzoic acid; trans-4-[α-hydroxyoctyloxyimino-(5,6,7,8-tetrahydro-5,5,8,8-tetramethyl-2-naphthyl)acetamido]benzoic acid; syn-4-[α-hydroxyheptyloxyimino-(5,6,7,8-tetrahydro-5,5,8,8-tetramethyl-2-naphthyl)acetamido]-benzoicacid;trans-4-[α-hydroxyheptyloxyimino-(5,6,7,8-tetrahydro-5,5,8,8-tetramethyl-2-naphthyl)acetamido]benzoic acid; syn-4-[α-hydroxypropyloxyimino-(5,6,7,8-tetrahydro-5,5,8,8-tetramethyl-2-naphthyl)acetamido]benzoic acid; trans-4-[α-hydroxy-propyloxyimino-(5,6,7,8-tetrahydro-5,5,8,8-tetramethyl-2-naphthyl)acetamido]benzoic acid; syn-4-[α-ethoxycarbonylpropyloxyimino-(5,6,7,8-tetrahydro-5,5,8,8-tetramethyl-2-naphthyl)acetamido]benzoic acid; syn-4-[α-hydroxydecyloxyimino-(5,6,7,8-tetrahydro-5,5,8,8-tetramethyl-2-naphthyl)acetamido]benzoic acid; syn-4-[α-hydroxynonyloxyimino-(5,6,7,8-tetrahydro-5,5,8,8-tetramethyl-2-naphthyl)acetamido]benzoic acid; syn-4-[α-benzyloxyimino-(5,6,7,8-tetrahydro-5,5,8,8-tetramethyl-2-naphthyl)acetamido]benzoic acid; syn-4-[α-methoxyethoxymethoxyimino-(5,6,7,8-tetrahydro-5,5,8,8-tetramethyl-2-naphthyl)acetamido]benzoic acid; allyl syn-4-[α-ethoxycarbonylpropyloxyimino-(5,6,7,8 -tetrahydro-5,5,8,8-tetramethyl-2-naphthyl)acetamido]benzoate; (E)-4-[2-(5,6,7,8-tetrahydro-5,5,8,8-tetramethyl-2-naphthyl)-2-nonenamido]benzoic acid; (Z)-4-[2-(5,6,7,8-tetrahydro-5,5,8,8-tetramethyl-2-naphthyl)-2-nonenamido]benzoic acid; (E)-4-[2-(5,6,7,8-tetrahydro-5,5,8,8-tetramethyl-2-naphthyl)-2-undecenamido]benzoic acid; (E)-4-[2-(5,6,7,8-tetrahydro-5,5,8,8-tetramethyl-2-naphthyl)-2-undecenamido]phenylcarboxamide; (E)-4-[2-(5,6,7,8-tetrahydro-5,5,8,8-tetramethyl-2-naphthyl)-2-undecenamido]-benzenemethanol; (E)-4-[2-(5,6,7,8-tetrahydro-5,5,8,8-tetramethyl-2-naphthyl)-2-undecenamido]phenol; (Z)-4-[2-(5,6,7,8-tetrahydro-5,5,8,8-tetramethyl-2-naphthyl)-2-undecenamido]benzoic acid; (E)-4-[2-(5,6,7,8-tetrahydro-5,5,8,8-tetramethyl-2-naphthyl)-2-hexadecenamido]benzoic acid; and (Z)-4-[2-(5,6,7,8-tetrahydro-5,5,8,8-tetramethyl-2-naphthyl)-2-hexadecenamido]benzoic acid.

21. A method for treating a dermatological, rheumatic, respiratory, cardiovascular or ophthalmological disorder in a mammalian organism in need of such treatment comprising administering a therapeutically effective amount of at least one biaromatic amide compound having the following structure:

(I)

in which Ar is a radical (a):

(a)

in which $R_5$ and $R_6$ are as defined below; Z is —CO—$NR_7$—; $R_1$ is (i) a —$CH_3$ radical, (ii) a radical —$CH_2$—O—$R_6$, (iii) a radical —O—$R_6$, (iv) a radical —CO—$R_8$ or (v) a radical —$S(O)_tR_9$, wherein $R_6$, $R_8$, $R_9$ and t are as defined below; X and Y may be taken separately, in which event X is a hydrogen atom or a lower alkyl radical, and Y is a radical of the formula —$(CH_2)_n$—$CH_3$ or of the formula —$(CH_2)_n$—$R_{10}$, or X and Y may be taken together, in which event X and Y together form, with the carbon atom from which they depend, a single radical containing a double bond, selected from among those of the formulae =N—O—$(CH_2)_n$—$R_{10}$, =CH—$(CH_2)_m$—$R_{10}$, =N—O—$(CH_2)_2$—O—$CH_2$—$CH_3$, =N—O—$CH_2$—O—$CH_2$—$CH_2$—O—$CH_3$ and =CH—$(CH_2)_m$—$CH_3$, wherein $R_{10}$, m and n are as defined below; $R_2$ and $R_3$, taken separately, are each a hydrogen atom, a linear or branched alkyl radical having from 1 to 20 carbon atoms, a radical —$OR_6$ or a radical —$SR_6$, wherein $R_6$ is as defined below, with the proviso that $R_2$ and $R_3$ cannot simultaneously be a hydrogen atom, a radical —$OR_6$ or a radical —$SR_6$, or $R_2$ and $R_3$ together form, with the adjacent aromatic ring from which they depend, a 5- or 6-membered ring optionally substituted by methyl radicals and/or optionally interrupted by an oxygen or sulfur atom or by an —SO— or —$SO_2$— radical; $R_4$ is a hydrogen atom, a halogen atom, a lower alkyl radical or a radical —$OR_6$, wherein $R_6$ is as defined below, with the proviso that $R_5$ has the same definition as $R_4$; $R_6$ is a hydrogen atom, a linear or branched alkyl radical having from 1 to 20 carbon atoms or a radical —CO—$R_{11}$, wherein $R_{11}$ is as defined below; $R_7$ is a hydrogen atom or a lower alkyl radical; $R_8$ is (a) a hydrogen atom, (b) a lower alkyl radical, (c) a radical of the formula:

wherein R' and R" are as defined below, or (d) a radical $-OR_{12}$, wherein $R_{12}$ is as defined below; $R_9$ and $R_{11}$, which may be identical or different, are each a lower alkyl radical; $R_{10}$ is (i) a radical $-OR_6$, (ii) a radical $-CO-R_8$, (iii) a radical of the formula:

wherein R' and R" are as defined below, (iv) an optionally substituted aryl radical, (v) a heterocyclic radical, or (vi) a $C_3$ or $C_6$ cycloaliphatic radical; $R_{12}$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; R' and R", which may be identical or different, are each a hydrogen atom, a lower alkyl radical, a mono- or polyhydroxyalkyl radical, an optionally substituted aryl radical or an amino acid or peptide or sugar residue, with the proviso that R' and R" may together form, with the nitrogen atom from which they depend, a heterocycle; m is an integer ranging from 1 to 20; n is an integer ranging from 2 to 20; and t is an integer equal to 0, 1 or 2; or a pharmaceutically/cosmetically salt or geometric or optical isomer thereof, wherein said compound is comprised in a dermatologically or pharmaceutically acceptable carrier contained in a pharmaceutically acceptable carrier.

* * * * *